(12) United States Patent
Kunnen et al.

(10) Patent No.: US 9,910,171 B2
(45) Date of Patent: Mar. 6, 2018

(54) THIN FILM TRANSISTOR DETECTION SYSTEMS AND RELATED METHODS

(71) Applicants: George Kunnen, Chandler, AZ (US); David Allee, Phoenix, AZ (US)

(72) Inventors: George Kunnen, Chandler, AZ (US); David Allee, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 208 days.

(21) Appl. No.: 14/851,779

(22) Filed: Sep. 11, 2015

(65) Prior Publication Data

US 2016/0003953 A1    Jan. 7, 2016

Related U.S. Application Data

(63) Continuation of application No. PCT/US2014/024558, filed on Mar. 12, 2014.
(Continued)

(51) Int. Cl.
| | | |
|---|---|---|
| *G01T 3/08* | (2006.01) | |
| *H01L 27/12* | (2006.01) | |
| *H01L 27/144* | (2006.01) | |
| *H01L 29/423* | (2006.01) | |
| *H01L 31/115* | (2006.01) | |
| *G01N 15/14* | (2006.01) | |

(52) U.S. Cl.
CPC ............ *G01T 3/08* (2013.01); *H01L 27/1214* (2013.01); *H01L 27/1443* (2013.01);
(Continued)

(58) Field of Classification Search
CPC ........................................................ G01T 3/08
See application file for complete search history.

(56) References Cited

U.S. PATENT DOCUMENTS 5,811,809 A  *   9/1998  Smith .............. G01R 19/16523
                                                     250/336.1
8,319,191 B2    11/2012  Allee
(Continued)

FOREIGN PATENT DOCUMENTS

| WO | 2011135920 | 11/2011 |
| WO | 2011152322 | 12/2011 |
| WO | 2012021196 | 2/2012 |

OTHER PUBLICATIONS

K. Kaftanoglu et al., "Stability Of IZO And a-Si:H TFTs Processed At Low Temperature (200C)," Journal of Display Technology, vol. 7, No. 6, pp. 339-343 (Jun. 2011).
(Continued)

*Primary Examiner* — David Porta
*Assistant Examiner* — Hugh H Maupin
(74) *Attorney, Agent, or Firm* — Bryan Cave LLP

(57) ABSTRACT

Some embodiments include a system. The system includes a sensor device having a sensor element having a sensor output and an amplification element having at least one amplification stage, an amplifier input, and an amplifier output. The sensor output can be coupled to the amplifier input. Further, each amplification stage of the amplification stage(s) can have at least four thin film transistors, an input node, and an output node. Meanwhile, the sensor element can detect a physical quantity and/or an event and can provide an electric signal to the amplification element in response to detecting the physical quantity and/or the event, and the amplification element can amplify the electric signal received from the sensor element. Other embodiments of related systems and methods are also disclosed.

21 Claims, 12 Drawing Sheets

Related U.S. Application Data

(60) Provisional application No. 61/778,185, filed on Mar. 12, 2013.

(52) U.S. Cl.
    CPC ...... *H01L 29/42384* (2013.01); *H01L 31/115* (2013.01); *G01N 15/1431* (2013.01)

(56) References Cited

U.S. PATENT DOCUMENTS

| | | | | |
|---|---|---|---|---|
| 8,466,426 | B2* | 6/2013 | Frank | G01T 3/00 250/390.11 |
| 8,796,608 | B2 | 8/2014 | Lee et al. | |
| 2011/0284755 | A1 | 11/2011 | Stradins et al. | |
| 2012/0211660 | A1* | 8/2012 | Allee | G01T 3/06 250/362 |
| 2012/0280133 | A1 | 11/2012 | Kagey et al. | |
| 2015/0009341 | A1* | 1/2015 | Pahr | G01R 31/2829 348/187 |

OTHER PUBLICATIONS

M. Marrs et al., "Control Of Threshold Voltage And Saturation Mobility Using Dual-Active-Layer Device Based On Amorphous Mixed Metal-Oxide-Semiconductor on Flexible Plastic Substrates," IEEE Trans. On Electron Devices, vol. 58, No. 10, pp. 3428-3434 (Oct. 2011).

K. S. Karim & A. Nathan "Amorphous Silicon Active Pixel Sensor Readout Circuit For Digital Imaging", IEEE Trans. Electron Devices, vol. 50, No. 1, pp. 200-208 (2003).

E. H. Lee et al., "A Low-Noise Dual-Stage a-Si:H Active Pixel Sensor," IEEE Transactions on Electron Devices, vol. 59, No. 6, pp. 1679-1685 (Jun. 2012).

Kunnen et al., "Large Area Sensing Arrays For Detection of Thermal Neutrons", Nuclear Science Symposium and Medical Imaging Conf., pp. 156-161, (Oct.-Nov. 2012).

D. S. McGregor et al., "Design Considerations For Thin Film Coated Semiconductor Thermal Neutron Detectors-I: Basics Regarding Alpha Particle Emitting Neutron Reactive Films," Nuclear Instruments and Methods in Physics Research, pp. 272-308 (2003).

D. Maneuski et al., "Evaluation Of Silicon Monolithic APS As A Neutron Detector," IEEE Nuclear Science Symposium Conference Record, pp. 2383-2386 (Oct. 2008).

M. Farrier et al., "Very Large Area CMOS Active-Pixel Sensor For Digital Radiography," IEEE Transactions on Electron Devices, vol. 56, No. 11, pp. 2623-2631 (Nov. 2009).

Kunnen et al., "A TFT-Based, Multi-Stage, Active Pixel Sensor For Alpha Particle Detection," Electronics Letters, vol. 50, issue 9, pp. 705-706 (Apr. 2014).

International Search Report and Written Opinion for Int'l Pat. App. No. PCT/US2014/024558 dated Mar. 12, 2014.

\* cited by examiner

THIN FILM TRANSISTOR DETECTION SYSTEMS AND RELATED METHODS

CROSS-REFERENCE TO RELATED APPLICATIONS

This application is a continuation of International Patent Application Ser. No. PCT/US2014/024558, filed Mar. 12, 2014. International Patent Application Serial No. PCT/US2014/024558 claims the benefit of United States Provisional Patent Application Ser. No. 61/778,185, filed Mar. 12, 2013. International Patent Application Serial No. PCT/US2014/024558 and U.S. Provisional Patent Application Ser. No. 61/778,185 each are incorporated herein by reference in their entirety.

STATEMENT REGARDING FEDERALLY SPONSORED RESEARCH OR DEVELOPMENT

This invention was made with government support under 1140044 awarded by the National Science Foundation. The government has certain rights in the invention.

FIELD OF THE INVENTION

This invention relates to detection systems. In particular, this invention relates to particle detection systems and methods of providing the same.

DESCRIPTION OF THE BACKGROUND

Detection systems, particularly thin film detection systems, can be fundamental components in numerous modern technologies. However, conventional amplification circuitry implemented with such detection systems has relied on poorly scalable manufacturing techniques. Specifically, conventional detection systems are read out via external charge preamplification because conventional thin film semiconductor processing techniques produce either only N-type or P-type devices, making usual high-gain complimentary metal-oxide semiconductor amplification unfeasible. As a result, the gain of the pixels in conventional detection systems is limited. One solution to this challenge has been to scale up the surface area of the pixels. However, when the pixel surface area is increased, the capacitance associated with the larger detection diodes of the pixels increases as well. For a finite amplifier gain, the increasing capacitance limits the achievable signal strength. Additionally, as the detection diodes increase in size, detection accuracy also suffers due to the increased noise associated with the larger detection diodes of the pixels. Accordingly, thin film detection systems with cost effective scalable amplification circuitry are desirable.

BRIEF DESCRIPTION OF THE DRAWINGS

To facilitate further description of the embodiments, the following drawings are provided in which.

Figure 1:
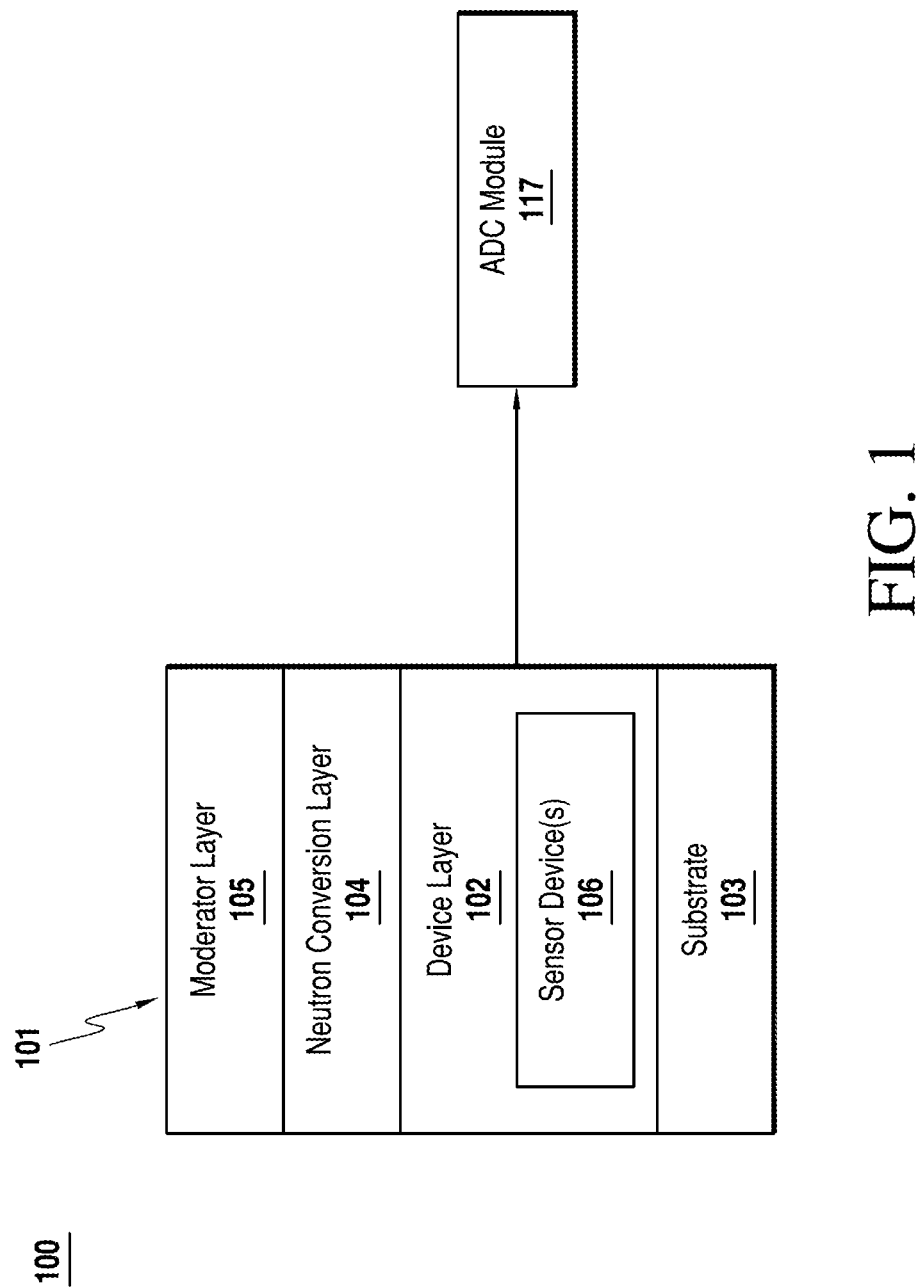
FIG. 1 illustrates a representative block diagram of a system, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments include a system. The system comprises a sensor device, and the sensor device comprises a sensor element comprising a sensor output, and an amplification element comprising at least one amplification stage, an amplifier input, and an amplifier output. The sensor output can be coupled to the amplifier input. Meanwhile, each amplification stage of the amplification stage(s) can comprise at least four thin film transistors, an input node, and an output node. Further, the sensor element can be configured to detect at least one of a physical quantity or an event and to provide an electric signal to the amplification element in response to detecting the at least one of the physical quantity or the event. Further still, the amplification element can be configured to amplify the electric signal received from the sensor element.

Other embodiments include a method of providing a system. The method comprises providing a sensor device. Meanwhile, providing the sensor device can comprise: providing a sensor element comprising a sensor output; providing an amplification element comprising an amplifier input and an amplifier output; and coupling the sensor output to the amplifier input. Further, providing the amplification element can comprise providing at least one amplification stage, and providing the at least one amplification stage can comprise providing at least four thin film transistors for each amplification stage of the at least one amplification stage. The sensor element can be configured to detect at least one of a physical quantity or an event and to provide an electric signal to the amplification element in response to detecting the at least one of the physical quantity or the event, and the amplification element can be configured to amplify the electric signal received from the sensor element.

Various embodiments include a system. The system comprises a flexible substrate and a device layer over the flexible substrate. The device layer comprises at least part of multiple sensor devices. Each sensor device of the multiple sensor devices comprises a sensor element comprising a sensor output and an amplification element comprising at least one amplification stage, an amplifier input, and an amplifier output. The at least the part of the multiple sensor devices can comprise the sensor element and the amplification element. Meanwhile, the sensor output can be coupled to the amplifier input. Further, each amplification stage of the amplification stage(s) can comprise an input node, an output node, and at least four N-type thin film transistors comprising a first N-type thin film transistor, a second N-type thin film transistor, a third N-type thin film transistor, and a fourth N-type thin film transistor. The sensor element can be configured to detect at least one of a physical quantity or an event and to provide an electric signal to the amplification element in response to detecting the at least one of the physical quantity or the event. Further, the amplification element can be configured to amplify the electric signal received from the sensor element.

In these embodiments, the sensor element can comprise a PIN diode, and each N-type thin film transistor of the at least four N-type thin film transistors comprises a gate, a source, and a drain. Meanwhile, for each amplification stage of the amplification stage(s): (i) the source of the third N-type thin film transistor can be coupled to the gate and the drain of the second N-type thin film transistor so that the second N-type thin film transistor and the third N-type thin film transistor are coupled in series with each other; (ii) the source of the second N-type thin film transistor can be coupled to the input node; (iii) the gate for the first N-type thin film transistor can be coupled to the input node; (iv) the drain for the third N-type thin film transistor can be coupled to the output node; and (v) the source for the fourth N-type thin film transistor can be coupled to the output node.

Further in these embodiments, the drain of the fourth N-type thin film transistor can be shorted to the gate of the fourth N-type thin film transistor. Likewise, a length of the gate of the fourth N-type thin film transistor can be longer than at least one of a length of the gate of the first N-type thin film transistor, a length of the gate of the second N-type thin film transistor, or a length of the gate of the third N-type thin film transistor. The amplification stage(s) can comprise three amplification stages coupled in series. Adjacent amplification stages of the three amplification stages each are coupled together in the series by at least one amplifier capacitor, respectively. Meanwhile, the three amplification stages can comprise a first amplification stage and a final amplification stage.

Still further in these embodiments, the amplifier input can comprise the input node of the first amplification stage, and the amplifier output can comprise the output node of the final amplification stage.

Turning to the drawings, FIG. 1 illustrates a representative block diagram of system 100, according to an embodiment. System 100 is merely exemplary and is not limited to the embodiments presented herein. System 100 can be employed in many different embodiments or examples not specifically depicted or described herein.

As discussed in greater detail herein, system 100 can be implemented where amplification of an electric signal is desirable. Accordingly, system 100 can be well suited for electronic detection application(s) having a sensor and/or related circuitry that generates electric signals. System 100 can be particularly well suited for electronic particle (e.g., neutron) detection via thin film semiconductor devices, such as, for example, to detect special nuclear material and/or for medical imaging.

Regardless of the manner of implementation, system 100 comprises semiconductor device 101 and one or more sensor device(s) 106, and semiconductor device 101 comprises device layer 102. In some embodiments, semiconductor device 101 can comprise substrate 103, neutron conversion layer 104, and/or moderator layer 105. In some embodiments, substrate 103, neutron conversion layer 104, and/or moderator layer 105 can be omitted. Further, system 100 can comprise analog-to-digital converter (ADC) module 117. In other embodiments, ADC module 117 can be omitted. Meanwhile, device layer 102 comprises at least part of each of sensor device(s) 106.

In applicable embodiments, moderator layer 105 can be in communication with (e.g., coupled with, contacting, and/or proximate to) neutron conversion layer 104, and neutron conversion layer 104 can be in communication with (e.g., coupled with, contacting, and/or proximate to) device layer 102. Meanwhile, in these or other embodiments, device layer 102 can be coupled (e.g., electronically) with ADC module 117. The functionality and interactions of moderator layer 105, neutron conversion layer 104, device layer 102, and ADC module 117 are described further below.

Substrate 103 can be configured to support device layer 102, neutron conversion layer 104, and/or moderator layer 105. Although substrate 103 generally can be implemented as any substrate (e.g., silicon) suitably configured to support device layer 102, neutron conversion layer 104, and/or moderator layer 105, in many embodiments, substrate 103 comprises a flexible substrate. The flexible substrate can comprise a plastic material, a metal foil material, and/or glass (e.g., Corning® glass, Willow™ glass, etc.). Implementing substrate 103 as a flexible substrate can be advantageous for various reasons. From a manufacturing standpoint, using a flexible substrate for substrate 103 can permit overlying semiconductor device layer(s) (e.g., device layer 102, neutron conversion layer 104, and/or moderator layer 105) to be cost effectively scaled to an appropriate surface area to accommodate the amplification element(s) of sensor device(s) 106 (e.g., amplification element 209 (FIG. 2)) as particularly implemented. Further, from an operability standpoint, using a flexible substrate for substrate 103 permits semiconductor device 101 to be rugged, conformal, and/or light weight, permitting wider deployment in the field. In these embodiments, because semiconductor device 101 is conformal, semiconductor device 101 can be conformed to partially or completely surround a patient during medical imaging. Still, in other embodiments, substrate 103 can comprise a rigid substrate.

The term "flexible substrate" as used herein means a free-standing substrate which readily adapts its shape. Accordingly, in many embodiments, the flexible substrate can comprise (e.g., consist of) a flexible material, and/or can comprise a thickness (e.g., an average thickness) that is sufficiently thin so that the substrate readily adapts in shape. In these or other embodiments, a flexible material can refer to a material having a low elastic modulus. Further, a low elastic modulus can refer to an elastic modulus of less than approximately five GigaPascals (GPa). In some embodiments, a substrate that is a flexible substrate because it is sufficiently thin so that it readily adapts in shape, may not be a flexible substrate if implemented with a greater thickness, and/or the substrate may have an elastic modulus exceeding five GPa. For example, the elastic modulus could be greater than or equal to approximately five GPa but less than or equal to approximately twenty GPa, fifty GPa, seventy GPa, or eighty GPa. Exemplary materials for a substrate that is a flexible substrate because it is sufficiently thin so that it readily adapts in shape, but that may not be a flexible substrate if implemented with a greater thickness, can comprise certain glasses (e.g., Corning® glass, Willow™ glass, etc.).

Meanwhile, the term "rigid substrate" as used herein can mean a free-standing substrate that does not readily adapt its shape and/or a substrate that is not a flexible substrate. In some embodiments, the rigid substrate can be devoid of flexible material and/or can comprise a material having an elastic modulus greater than the elastic modulus of a flexible substrate. In various embodiments, the rigid substrate can be implemented with a thickness that is sufficiently thick so that the substrate does not readily adapt its shape. In these or other examples, the increase in rigidity of the carrier substrate provided by increasing the thickness of the carrier substrate can be balanced against the increase in cost and weight provided by increasing the thickness of the carrier substrate.

Regarding device layer 102 and sensor device(s) 106, each sensor device of sensor device(s) 106 can be operable as an active pixel sensor. When sensor device(s) 106 comprise multiple sensor devices, at least part of sensor device(s) 106 (e.g., active pixel(s) of sensor device(s) 106) can be arranged at device layer 102 such that device layer 102 comprises and is operable as an active pixel sensor array.

Figure 2:
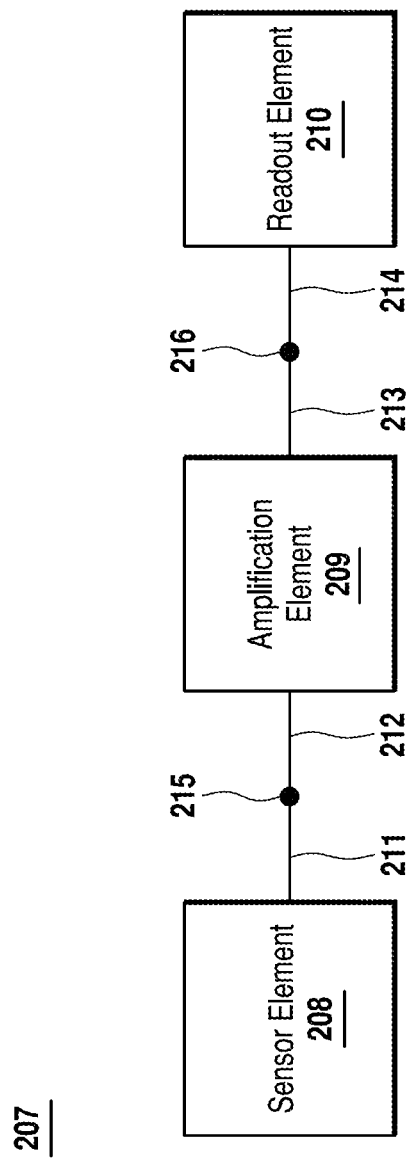
FIG. 2 illustrates a representative block diagram of a sensor device, according to the embodiment of FIG. 1.

Referring to the next drawing, FIG. 2 illustrates a representative block diagram of sensor device 207, according to the embodiment of FIG. 1. Each sensor device of sensor device(s) 106 can be similar or identical to sensor device 207.

Sensor device 207 comprise sensor element 208, amplification element 209, and readout element 210. Sensor element 208 and amplification element 209 can provide an active pixel of sensor device 207. In some embodiments, at least part of readout element 210 can be part of the active pixel. However, in other embodiments, readout element 210 is separate from the active pixel. Further, sensor element 208 comprises sensor output 211, amplification element 209 comprises amplifier input 212 and amplifier output 213, and readout element 210 comprises readout input 214. Sensor element 208 is coupled to amplification element 209, and amplification element 209 is coupled to readout element 210. For example, sensor output 211 can be coupled to amplifier input 212 at node 215, and amplifier output 213 can be coupled to readout input 214 at node 216.

Sensor element 208 is configured to detect a physical quantity, which may include a change therein, and/or an event and to provide an electric signal to amplification element 209 in response to detecting the physical quantity and/or the event. Exemplary physical quantities can comprise charge, temperature, pressure, and/or force, etc. Meanwhile, exemplary events can comprise receipt of electromagnetic radiation (e.g., ionizing radiation) at sensor element 208. Accordingly, in many embodiments, sensor element 208 can comprise a PIN diode and/or a photodiode. In these embodiments, sensor output 211 can comprise a cathode of the diode. In other embodiments, sensor element 208 can comprise any other suitable sensor configured to detect a physical quantity and/or an event and to generate an electric signal in response thereto.

Meanwhile, amplification element 209 is configured to receive the electric signal from sensor element 208 and to amplify the electric signal to a sufficient voltage level to be detected over any interfering noise. For example, amplification element 209 can be configured to amplify the electric signal to a voltage level of greater than or equal to approximately 100 millivolts.

Figure 3:
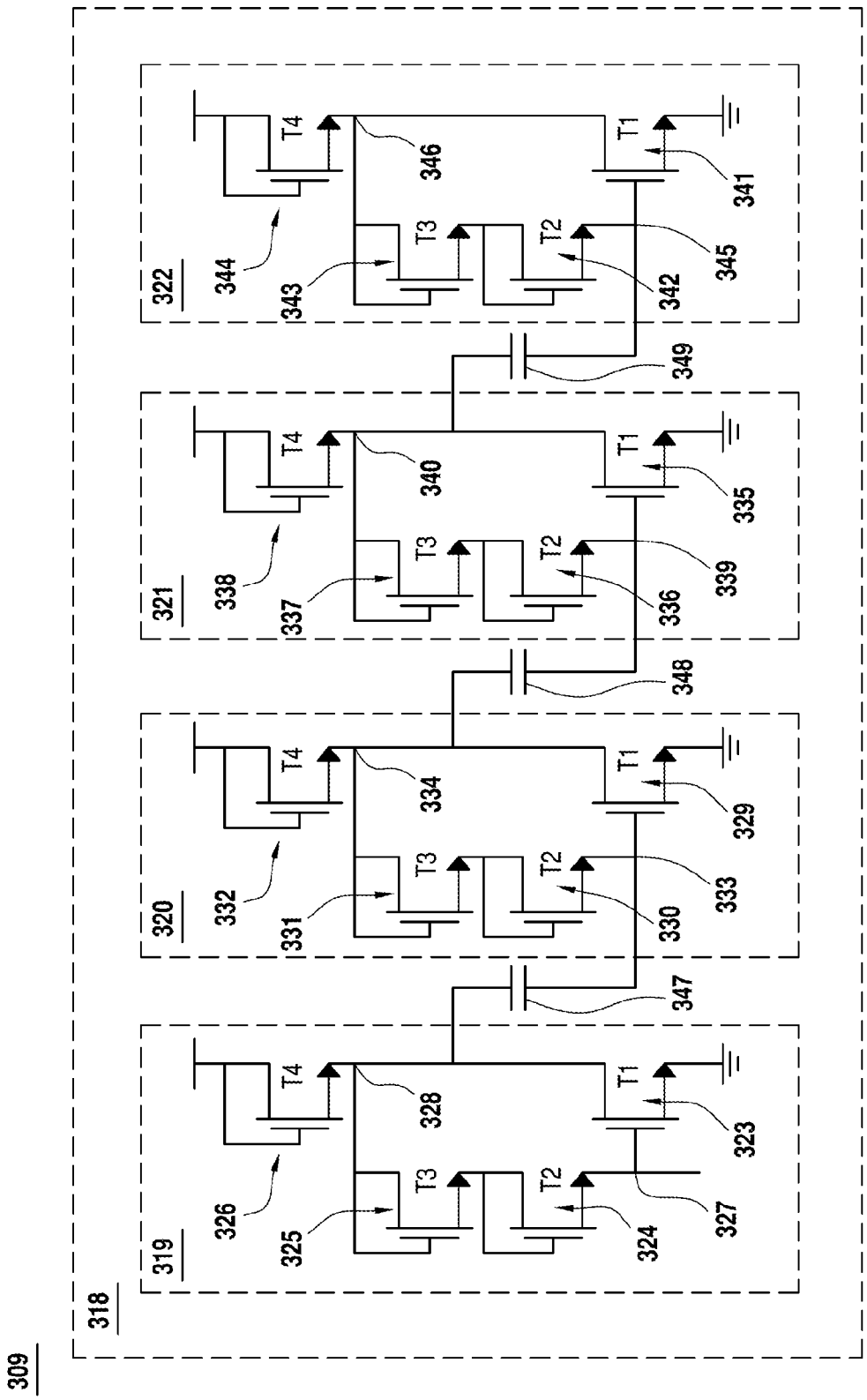
FIG. 3 illustrates a circuit diagram for an amplification element with four amplification stages, according to the embodiment of FIG. 1.

In implementation, amplification element 209 comprises at least one amplification stage 218. In specific examples, amplification element 209 can comprise three or four amplification stages. Each amplification stage of amplification stage(s) 218 can be similar or identical to each other, cascaded, and/or common sourced. Further, each amplification stage of amplification stage(s) 218 can comprise at least four thin film transistors (e.g., N-type thin film transistors), an input node, and an output node. Meanwhile, each thin film transistor (N-type thin film transistor) comprises a gate, a source, and a drain. FIG. 3 illustrates a circuit diagram for amplification element 309 with four amplification stages, according to the embodiment of FIG. 1. Amplification element 209 (FIG. 2) can be similar or identical to amplification element 309.

Amplification element 309 comprises amplification stage(s) 318, first amplifier capacitor 347, second amplifier capacitor 348, and third amplifier capacitor 349. Meanwhile, amplification stage(s) 318 comprise first amplification stage 319, second amplification stage 320, third amplification stage 321, and fourth amplification stage 322. In many embodiments, when amplification stage(s) 318 comprise multiple amplification stages, amplification stage(s) 318 can be coupled in series with each other. In these or other embodiments, adjacent amplification stages each can be coupled together in the series by (e.g., isolated from each other by) at least one capacitor (e.g., first amplifier capacitor 347, second amplifier capacitor 348, third amplifier capacitor 349, etc.). In many embodiments, the capacitor(s) can comprise alternating current capacitor(s). For reference, the last amplification stage in the series (e.g., fourth amplification stage 322) can be referred to as the "final amplification stage."

In these or other embodiments, first amplification stage 319 can comprise first N-type thin film transistor 323, second N-type thin film transistor 324, third N-type thin film transistor 325, and fourth N-type thin film transistor 326, input node 327, and output node 328. Meanwhile, second amplification stage 320 can comprise first N-type thin film transistor 329, second N-type thin film transistor 330, third N-type thin film transistor 331, and fourth N-type thin film transistor 332, input node 333, and output node 334; third amplification stage 321 can comprise first N-type thin film transistor 335, second N-type thin film transistor 336, third N-type thin film transistor 337, and fourth N-type thin film transistor 338, input node 339, and output node 340; and fourth amplification stage 322 can comprise first N-type thin film transistor 341, second N-type thin film transistor 342, third N-type thin film transistor 343, and fourth N-type thin film transistor 344, input node 345, and output node 346.

Further in these embodiments, amplifier input 212 can comprise input node 327, and amplifier output 213 can comprise output node 346. Amplifier input 212 and/or input node 327 can be referred to as the "sensitive node." Meanwhile, output node 328 can be coupled to input node 333 by first amplifier capacitor 347, output node 334 can be coupled to input node 339 by second amplifier capacitor 348, and output node 340 can be coupled to input node 345 by third amplifier capacitor 349.

For purposes of brevity, only the configuration of first amplification stage 319 is described in detail, but as a general matter: (i) first N-type thin film transistor 329, first N-type thin film transistor 335, and first N-type thin film transistor 341 can be similar or identical to first N-type thin film transistor 323, (ii) second N-type thin film transistor 330, second N-type thin film transistor 336, and second N-type thin film transistor 342 can be similar or identical to second N-type thin film transistor 324, (iii) third N-type thin film transistor 331, third N-type thin film transistor 337, and third N-type thin film transistor 343 can be similar or identical to third N-type thin film transistor 325, (iv) fourth N-type thin film transistor 332, fourth N-type thin film transistor 338, and fourth N-type thin film transistor 344 can be similar or identical to fourth N-type thin film transistor 326, (v) input node 333, input node 339, and input node 345 can be similar or identical to input node 327; and (vi) output node 334, output node 340, and output node 346 can be similar or identical to output node 328.

Focusing now on first amplification stage 319, amplifier input 212 (FIG. 2) and input node 327 can be self-biased in a direct current regime by second N-type thin film transistor 324 and third N-type thin film transistor 325. For example, second N-type thin film transistor 324 and third N-type thin film transistor 325 can be coupled in series with each other. Specifically, the source of third N-type thin film transistor 325 can be coupled to the gate and the drain of second N-type thin film transistor 324, the source of second N-type thin film transistor 324 can be coupled to input node 327, and the drain of third N-type thin film transistor 325 can be coupled to output node 328.

Meanwhile, the gate of first N-type thin film transistor 323 can be coupled to input node 327, and the source of fourth N-type thin film transistor 326 can be coupled to output node 328. Further, the gate and the drain of fourth N-type thin film transistor 326 can be coupled to a power node of system 100 (FIG. 1) and/or semiconductor device 101 (FIG. 1), and the source of first N-type thin film transistor 323 can be coupled to a ground node of system 100 (FIG. 1) and/or semiconductor device 101 (FIG. 1). The power node can electrically power first amplification stage 319. Accordingly, in these or other embodiments, the drain of fourth N-type thin film transistor 326 can be shorted to the gate of fourth N-type thin film transistor 326.

In many embodiments, a length of the gate of fourth N-type thin film transistor 326 can be longer than a length of the gate of first N-type thin film transistor 323, a length of the gate of second N-type thin film transistor 324, and/or a length of the gate of the third N-type thin film transistor 325.

Amplifier stage(s) 318 can operate as follows. First, amplifier input 212 (FIG. 2) and input node 327 can receive the electric signal from sensor element 208. First amplification stage 319 amplifies the electric signal as a result of the amplifier load created by the drain of fourth N-type thin film transistor 326 being shorted to the gate of fourth N-type thin film transistor 326. Configuring the length of the gate of fourth N-type thin film transistor 326 to be longer than the length(s) of the gate(s) of first N-type thin film transistor 323, second N-type thin film transistor 324, and/or third N-type thin film transistor 325 improves the gain provided by shorting fourth N-type thin film transistor 326. After the electric signal is amplified at first amplification stage 319, the electric signal passes to each subsequent amplification stage (e.g., second amplification stage 320, third amplification stage 321, fourth amplification stage 322, etc.) for further amplification.

Because amplifier input 212 (FIG. 2) and input node 327 are self-biased, amplifier input 212 (FIG. 2) and input node 327 can slowly "reset" to a high-gain direct current operating point after the voltage is changed at amplifier input 212 (FIG. 2) and input node 327 due to sensor element 208 passing the electric signal to amplifier input 212 (FIG. 2) and input node 327. Meanwhile, as the input node (e.g., input node 333, input node 339, input node 345, etc.) of each subsequent amplification stage (e.g., second amplification stage 320, third amplification stage 321, fourth amplification stage 322, etc.) is self-biased in similar manner to amplifier input 212 (FIG. 2) and input node 327, a correct direct current bias of the input node (e.g., input node 333, input node 339, input node 345, etc.) of each subsequent amplification stage (e.g., second amplification stage 320, third amplification stage 321, fourth amplification stage 322, etc.) can be maintained by first amplifier capacitor 347, second amplifier capacitor 348, and third amplifier capacitor 349, respectively, while still passing a high frequency electric signal. Specifically, first amplifier capacitor 347, second amplifier capacitor 348, and third amplifier capacitor 349 can act as short circuits between adjacent amplification stage(s) of amplification stage(s) 318 when receiving high frequency electric signals and as open circuits between adjacent amplification stage(s) of amplification stage(s) 318 when receiving low frequency electric signals. Each amplification stage of amplification stage(s) 318 can provide greater than or equal to approximately 3 volt/volt of gain and less than or equal to approximately 4 volt/volt of gain. However, the gain of the electrical signal increases exponentially for each amplification stage of amplification stage(s) 318 that is implemented. For example, when implementing four amplification stages of amplification stage(s) 318, the resulting gain can comprise approximately 200 volt/volt of gain.

Referring briefly back to FIG. 2, after passing through the various amplification stage(s) of amplification stage(s) 318 (FIG. 3), the amplified electric signal can be readout via readout element 210. Readout element 210 can be configured to read the electric signal provided by amplification element 209 in either a voltage mode or a current mode.

Figure 4:
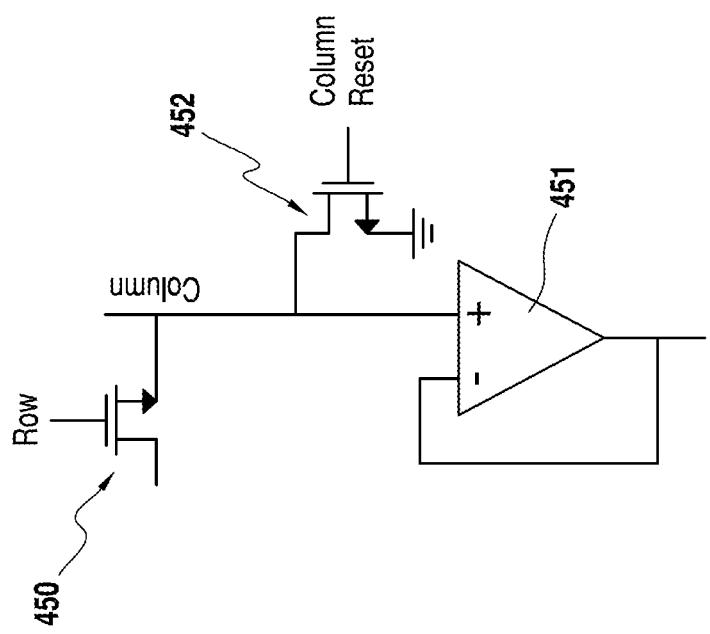
FIG. 4 illustrates a circuit diagram for an exemplary readout element, according to the embodiment of FIG. 1.
Figure 5:
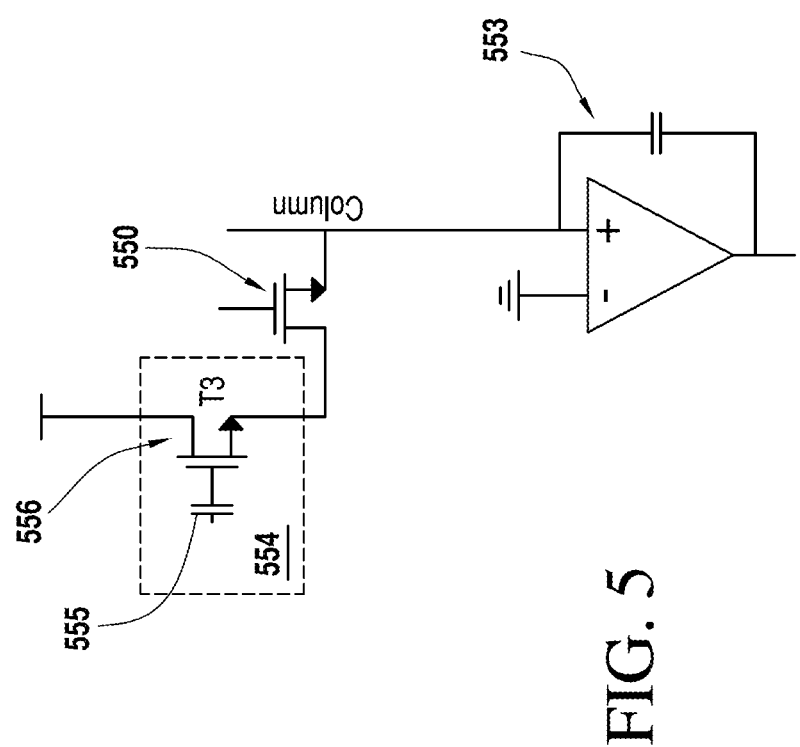
FIG. 5 illustrates a circuit diagram for another exemplary readout element, according to the embodiment of FIG. 1.

Turning ahead in the drawings, FIG. 4 illustrates a circuit diagram for readout element 410, according to the embodiment of FIG. 1, and FIG. 5 illustrates a circuit diagram for readout element 510, according to the embodiment of FIG. 1. Readout element 210 (FIG. 2) can be similar or identical to readout element 410 (FIG. 4) or readout element 510 (FIG. 5). As explained in greater detail below, when readout element 210 is implemented to be similar or identical to readout element 410, sensor device(s) 106 can be configured to be readout in a voltage mode, and when readout element 210 is implemented to be similar or identical to readout element 510, sensor device(s) 106 can be configured to be readout in a current mode.

Referring now to FIG. 4, readout element 410 can comprise row access transistor 450, unity gain buffer 451, and column reset transistor 452. Unity gain buffer 451 and column reset transistor 452 can be coupled to row access transistor 450. For example, a voltage input of unity gain buffer 451, a drain of column reset transistor 452 can be coupled to a source of row access transistor 450, and a source of column reset transistor 452 can be coupled to the ground node of system 100 (FIG. 1). Meanwhile, in these embodiments, readout input 214 (FIG. 2) can comprise a drain of row access transistor 450.

In operation, row access transistor 450 can be operated according to conventional techniques for selectively reading out an active sensor pixel array (e.g., of device layer 102 (FIG. 1)) in a voltage mode. For example, when row access transistor is activated, the amplified electric signal provided by amplifier element 209 (FIG. 2) can be directly fed into a column output line to be provided to unity gain buffer 451. Meanwhile, column reset transistor 452 can be configured to reset the column line to 0 volts before a subsequent sensor device of sensor device(s) 106 (FIG. 1) is readout on the same column line. This prevents any previous voltages on the column line from affecting the operation of other sensor device(s) of sensor device(s) 106 that are readout via the same column output line.

Upon receiving the electric signal, unity gain buffer 451 can provide the amplified electric signal to ADC module 117 (FIG. 1). In these embodiments, a voltage output of unity gain buffer 451 can be coupled to ADC module 117 (FIG. 1). In many embodiments, unity gain buffer 451 and ADC module 117 (FIG. 1) can be separate from semiconductor device 101 (FIG. 1) and/or device layer 102 (FIG. 1). In these or other embodiments, ADC module 117 can be configured to operate in accordance with the conventional functionality of an analog-to-digital converter.

Meanwhile, referring to FIG. 5, readout element 510 can comprise row access transistor 550, current integrator 553, and source follower element 554. Meanwhile, source follower element 554 can comprise source follower element capacitor 555 and source follower transistor 556. Row access transistor 550 can be similar or identical to row access transistor 450 (FIG. 4).

In these embodiments, readout input 214 (FIG. 2) can comprise a voltage input of source follower element capacitor 555. Meanwhile, source follower element capacitor 555 can be coupled to source follower transistor 556, and source follower transistor 556 can be coupled to current integrator 553. For example, a voltage output of source follower element capacitor 555 can be coupled to a gate of source follower transistor 556, a drain of source follower transistor 556 can be coupled to the power node of system 100 (FIG. 1) and/or semiconductor device 101 (FIG. 1), and a source of source follower transistor 556 can be coupled to a drain of row access transistor 550. Further, a gate of row access transistor 550 can be coupled to the power node of system 100 (FIG. 1) and/or semiconductor device 101 (FIG. 1), and a source of row access transistor 550 can be coupled to a voltage input of current integrator 553.

In operation, amplifier element 209 (FIG. 2) can pass the amplified electric signal to source follower element 554. For example, in many embodiments, the high frequency amplified electric signal provided by amplifier element 209 (FIG. 2) first can pass though source follower element capacitor 555. Then, the amplified electric signal can pass from source follower element capacitor 555 to source follower transistor 556. Row access transistor 550 can be similar or identical to row access transistor 450 (FIG. 4). Accordingly, row access transistor 550 can be operable to selectively pass the amplified electric signal from source follower transistor 556 to a column output line to be provided to current integrator 553. The output column line can be connected to a virtual ground of current integrator 553. In these embodiments, it is not necessary to reset a voltage of the output column line after reading out the electric signal.

Further in these embodiments, a voltage output of current integrator 553 can be coupled to ADC module 117 (FIG. 1). Thus, current integrator 553 can pass electric signals provided by amplifier element 209 (FIG. 2) to ADC module 117 (FIG. 1).

Referring now back to FIG. 1, when semiconductor device 101, device layer 102, and/or sensor device(s) 106 are implemented to detect special nuclear material, semiconductor device 101 (e.g., at moderator layer 105) can be configured to receive neutrons (e.g., fast neutrons) from special nuclear material and to intercept, scatter, and/or thermalize the neutrons. Meanwhile, neutron conversion layer 104 can be configured to capture the slowed neutrons and to emit ionizing radiation (e.g., alpha particles) as a result of capturing the thermal neutrons. Device layer 102 and/or sensor device(s) 106 can then either directly or indirectly detect the ionizing radiation, which can be associated with thermal neutron flux, which in turn can be associated with a presence of special nuclear material. In embodiments where device layer 102 and/or sensor devices 106 detect the ionizing radiation indirectly, semiconductor device 101 can comprise a scintillator layer configured to first receive the ionizing radiation and luminesce, in which case device layer 102 and/or sensor device(s) 106 can be configured to detect the luminescence to detect the ionizing radiation.

Moderator layer 105 can comprise any material suitable for intercepting, scattering, and/or thermalizing a neutron. For example, in some embodiments, moderator layer 105 can comprise paraffin. Meanwhile, neutron conversion layer 104 can comprise any material configured to capture a neutron. Exemplary material(s) for neutron conversion layer 104 can comprise 10-Boron or 6-Lithium. Accordingly, when neutron conversion layer 104 comprises 10-Boron material, neutron conversion layer 104 can emit alpha particles in a forward direction according to a $^{10}B(n,\alpha)^7Li$ reaction.

Device layer 102 (e.g., part of sensor device(s) 106), neutron conversion layer 104, and/or moderator layer 105 can be provided (e.g., over substrate 103) according to any suitable semiconductor (e.g., thin film semiconductor) manufacturing techniques. For example, in many embodiments, at least part of device layer 102 and/or sensor device(s) 106 (e.g., amplifier element 318 (FIG. 3)) can be provided using aSi:H or InGaZnO semiconductor manufacturing techniques. The following references describe semiconductor manufacturing techniques that can be implemented to provide at least part of device layer 102 and/or sensor device(s) 106 (e.g., amplifier element 318 (FIG. 3)): (i) K. Kaftanoglu, S. M. Venugopal, M. Marrs, A. Dey, E. J. Bawolek, D. R. Allee, D. Loy, "Stability of IZO and a-Si:H TFTs Processed at Low Temperature (200)," Journal of Display Technology, vol. 7, no. 6, pp. 339-343, June 2011; and (ii) M. A. Mans, C. D. Moyer, E. J. Bawolek, R. J. Cordova, J. Trujillo, G. B. Raupp, B. D. Vogt, "Control of Threshold Voltage and Saturation Mobility Using Dual-Active-Layer Device Based on Amorphous Mixed Metal-Oxide-Semiconductor on Flexible Plastic Substrates," IEEE Transactions on Electron Devices, vol. 58, no. 10, pp. 3428-3434, October 2011, both of which are incorporated herein by reference in their entirety.

Further, U.S. patent application Ser. No. 13/298,451, published as United States Patent Application Publication Serial Number US20120061672 and filed on Nov. 17, 2011, describes various other embodiments of semiconductor manufacturing techniques suitable for providing device layer 102 (e.g., part of sensor device(s) 106), neutron conversion layer 104, and/or moderator layer 105. Further, International Patent Application Serial Number PCT/US2011/037207, published as International Patent Publication Serial Number WO2012021196 and filed May 19, 2011, also describes still other embodiments of semiconductor manufacturing techniques suitable for providing device layer 102 (e.g., part of sensor device(s) 106), neutron conversion layer 104, and/or moderator layer 105. U.S. patent application Ser. No. 13/298,451 and International Patent Application Ser. No. PCT/US2011/037207 are incorporated herein by reference in their entirety.

In many embodiments, device layer 102 can be located (e.g., deposited, such as, for example, sputtered) over substrate 103. In some embodiments, neutron conversion layer 104 can be located (e.g., deposited, such as, for example, sputtered) over device layer 102. In further embodiments, moderator layer 105 can be located (e.g., deposited, such as, for example, sputtered) over neutron conversion layer 104.

As discussed previously, system 100 can be implemented to detect special nuclear material. Detecting special nuclear material can be an important security tool. Because gamma backgrounds can be unpredictable, system 100 can advantageously focus on neutron detection in order detect the presence of special nuclear material. System 100 can be particularly advantageous because it does not rely on 3He to operate, the supply of which is expensive and dwindling, as do conventional neutron detection systems and because a demand for neutron detection is ever increasing. Meanwhile, because system 100 permits a surface area of device layer 102 to be cost effectively scaled up by increasing the total number of active pixel(s) of sensor device(s) 106 without increasing the size of the sensor element(s) of sensor device(s) 106, absolute detection efficiencies of system 100 can be increase beyond the efficiencies of conventional detection systems implementing neutron conversion layers, which are limited to intrinsic thermal neutron detection efficiencies of greater than or equal to approximately 4 percent and less than or equal to approximately 11 percent. Because the sensor element(s) of sensor device(s) 106 remain small, noise in system 100 is mitigated that would otherwise be caused by increasing the size of the sensor element(s).

Further, system 100 can be advantageous because the self biasing of the input node(s) (e.g., input node 327 (FIG. 3), input node 333 (FIG. 3), input node 339 (FIG. 3), input node 345 (FIG. 3), etc.) of amplification stage(s) 318 (FIG. 3) permits each amplification stage of amplification stage(s) 318 to automatically reset to a high gain state. Further still, for abrupt changes in charge at the input node(s) (e.g., input node 327 (FIG. 3), input node 333 (FIG. 3), input node 339 (FIG. 3), input node 345 (FIG. 3), etc.) of amplification stage(s) 318 (FIG. 3), the resulting waveform of the electric signal generated by sensor element 208 (FIG. 2) and amplified by amplifier element 209 (FIG. 2) will both represent an amplified pulse proportional to the original change in charge, and most importantly, the pulse will slowly decay back to the output direct current operating point. These advantages are illustrated by comparing FIGS. 6 & 7 to FIGS. 11 & 12.

Figure 6:
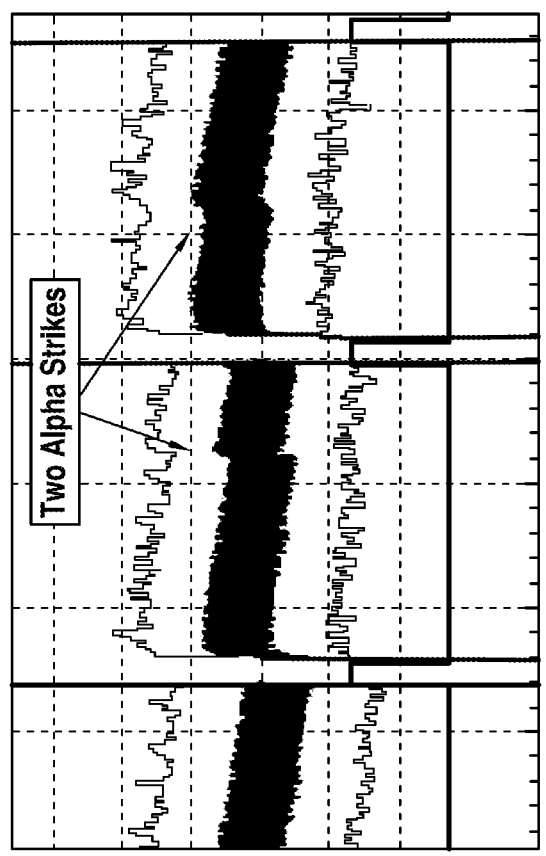
FIG. 6 illustrates a graphical representation of a conventional dual-stage detection system detecting a single alpha strike.
Figure 7:
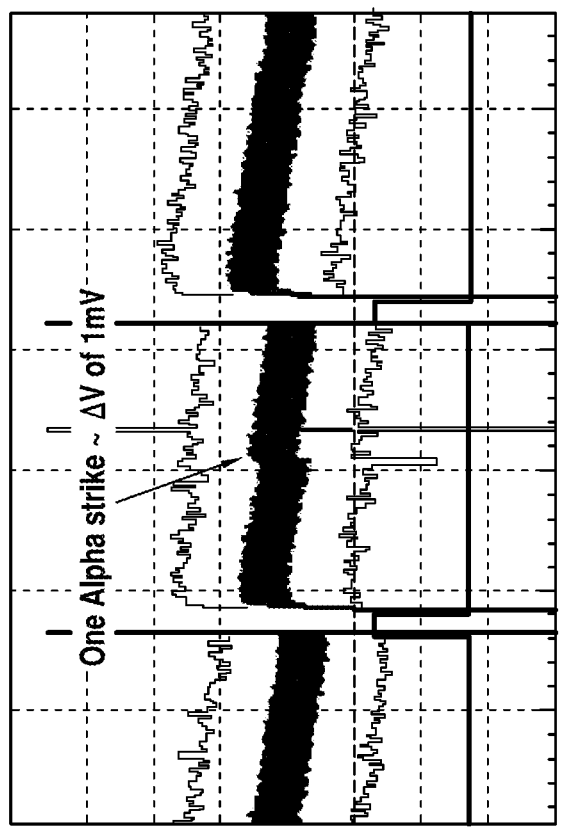
FIG. 7 illustrates a graphical representation of the conventional dual-stage detection system of FIG. 6 detecting two alpha strikes.
Figure 11:
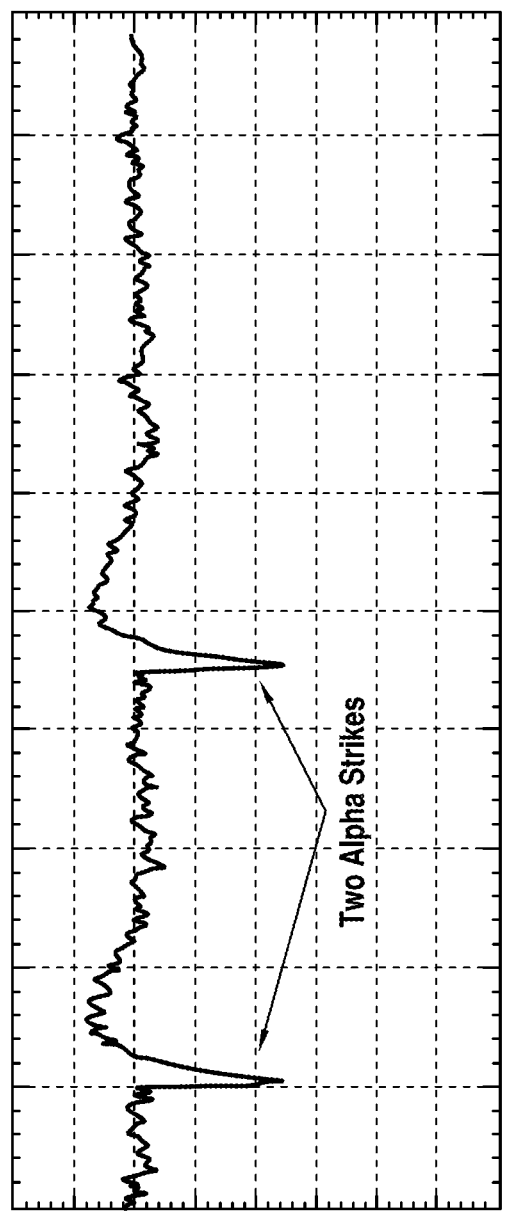
FIG. 11 illustrates a system corresponding to the system of FIG. 1 with four amplification stages in a voltage readout mode configuration detecting a single alpha strike.
Figure 12:
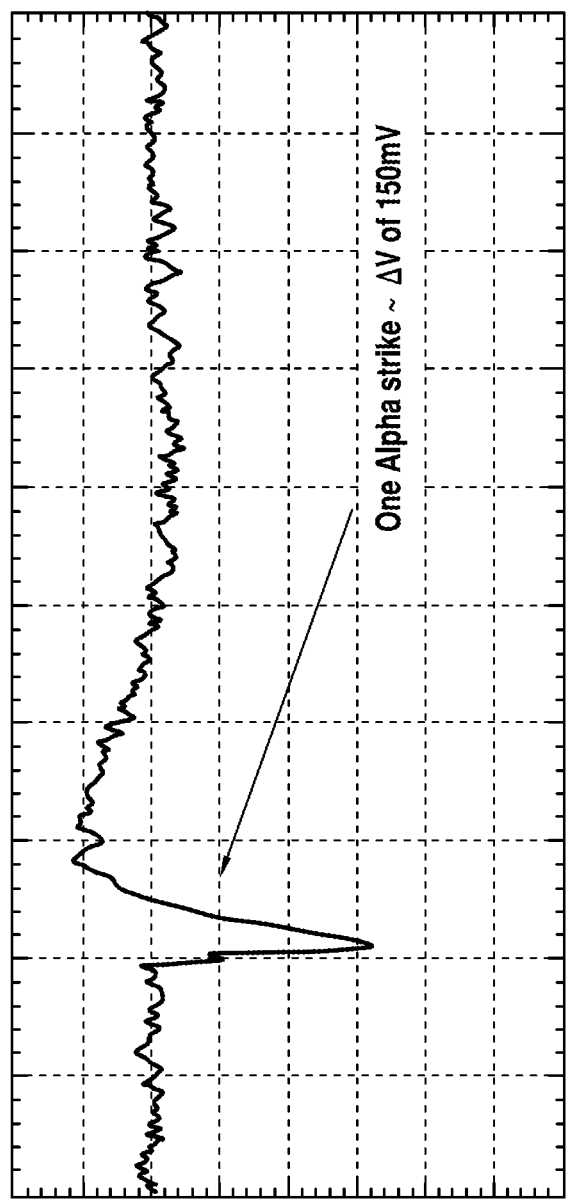
FIG. 12 illustrates the system of FIG. 11 detecting two alpha strikes.

FIG. 6 illustrates a graphical representation of a conventional dual-stage detection system detecting a single alpha strike. The dual-stage detection system is implemented as described in E. H. Lee, G. R. Kunnen, A. Dominguez, D. R. Allee, "A Low-Noise Dual-Stage a-Si:H Active Pixel Sensor," IEEE Transactions on Electron Devices, vol. 59, no. 6, pp. 1679-1685, June 2012. FIG. 7 illustrates a graphical representation of the conventional dual-stage detection system detecting two alpha strikes. By contrast, FIG. 11 illustrates a system with four amplification stages in a voltage readout mode configuration detecting a single alpha strike. The system can be similar or identical to system 100 (FIG. 1). Meanwhile, FIG. 12 illustrates the system of FIG. 11 detecting two alpha strikes. The graphical representations of FIGS. 6 & 7 are illustrated for a channel voltage of 5.00 millivolts and a time division of 2.00 milliseconds. Meanwhile, the graphical representations of FIGS. 11 & 12 are illustrated for a channel voltage of 50.0 millivolts with FIG. 11 having a peak-to-peak voltage of 180 millivolts, a room mean square voltage of 20.3 millivolts, a time division of 4.00 milliseconds, and a trigger slope of −28.0 millivolts and with FIG. 12 having a peak-to-peak voltage of 234 millivolts, a room mean square voltage of 27.8 millivolts, a time division of 2.00 milliseconds, and a trigger slope of −46.0 millivolts.

Comparing FIG. 6 to FIG. 11 and FIG. 7 to FIG. 12 shows that under the conventional dual-stage detection system of FIGS. 6 & 7, the output step(s) due to alpha strike(s) are almost buried in the noise floor. It should be noted that this is the case even after considerable measures were taken to decrease external noise sources in order to attain visible output step(s). Meanwhile, the output pulse(s) in the system of FIGS. 11 & 12 are clearly visible and the system did not require any corresponding noise reduction measures. Both the dual-stage detection system of FIGS. 6 & 7 and the system of FIGS. 11 & 12 used the same $^{210}Po$ source of special nuclear material and the same OPF480 PIN diode.

Figure 13:
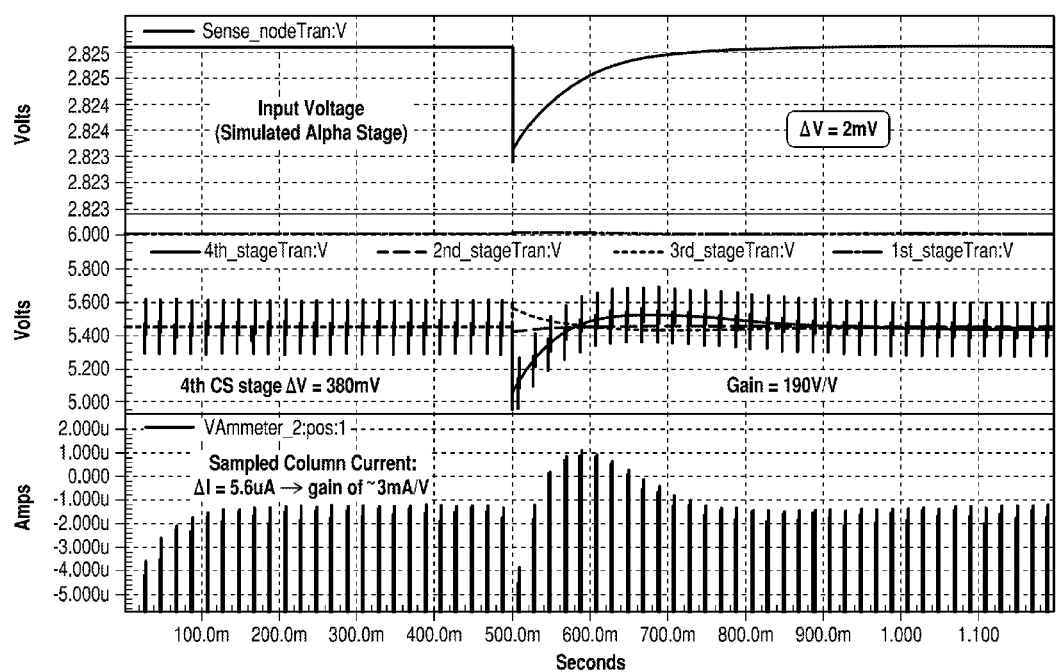
FIG. 13 illustrating a transient analysis of a system corresponding to the system of FIG. 1 with four amplification stages in a current readout mode configuration.

Meanwhile, the long "tail" at the output step(s) of the system of FIGS. 11 & 12 due to detecting an alpha strike is especially advantageous because it allows sampling to occur through multiple rows while still being able to "catch" parts of the output waveform. This capability is perhaps better shown at FIG. 13 illustrating a transient analysis of a system with four amplification stages in a current readout mode configuration. The system can be similar or identical to system 100 (FIG. 1). For example, an input is stimulated with a single small step in charge (representing an alpha strike), while the row signal is pulsed on and off with a very low duty cycle, in order to represent array operation (with multiple rows). It is clear that due to the elongated "tail" of the pulse at the output step(s) of the final amplification stages of the system, the sampled column output is still able to resolve the general shape of the alpha-induced pulse for a particular row.

Referring again back to FIG. 1, in some embodiments of system 100, it is helpful to employ layout techniques in order to avoid any parasitic feedback in system 100. When there are an even number of stages of amplification stage(s) 318, parasitic feedback along with high amplifier gain can cause instability due to positive feedback. In order to stabilize system 100, in some embodiments, a small resistance (~1 MOhm) can be applied from amplifier output 213 to ground. In other embodiments, an odd number of stages of amplification stage(s) 318 (FIG. 3) (along with careful layout techniques) can be implemented to ensure stable operation even in the presence of parasitic feedback in system 100 (FIG. 1).

Figure 8:
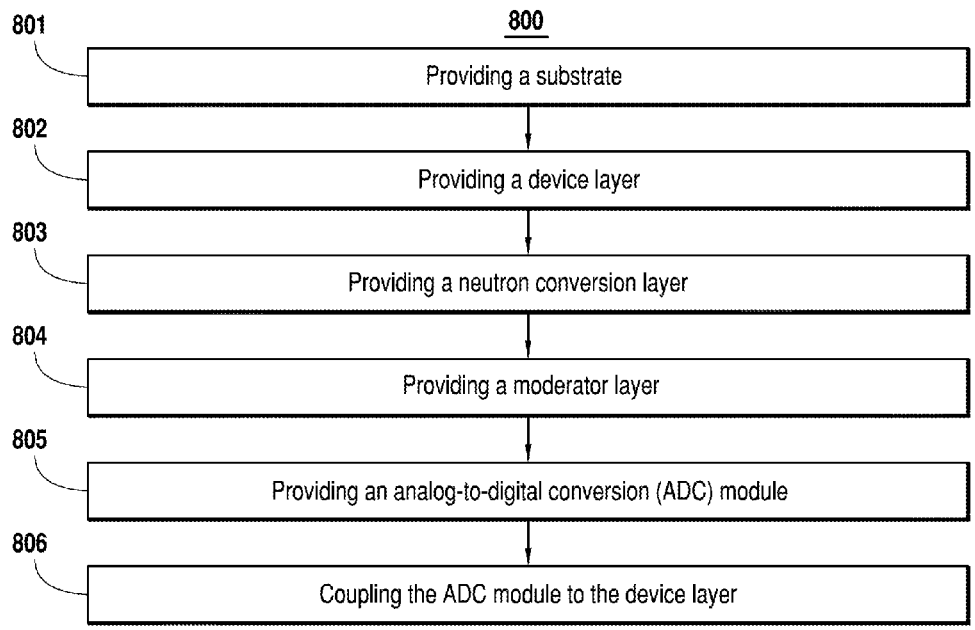
FIG. 8 illustrates a flow chart for an embodiment of a method of providing a system.

Turning ahead in the drawings, FIG. 8 illustrates a flow chart for an embodiment of method 800 of providing a system. Method 800 is merely exemplary and is not limited to the embodiments presented herein. Method 800 can be employed in many different embodiments or examples not specifically depicted or described herein. In some embodiments, the activities, the procedures, and/or the processes of method 800 can be performed in the order presented. In other embodiments, the activities, the procedures, and/or the processes of method 800 can be performed in any other suitable order. In still other embodiments, one or more of the activities, the procedures, and/or the processes in method 800 can be combined or skipped. The system can be similar or identical to system 100 (FIG. 1).

Method 800 can comprise activity 801 of providing a substrate. The substrate can be similar or identical to the flexible substrate described above with respect to system 100 (FIG. 1) and/or substrate 103 (FIG. 1). In some embodiments, activity 801 can be omitted.

Further, method 800 can comprise activity 802 of providing a device layer, such as, for example, over the substrate. The device layer can be similar or identical to device layer 102 (FIG. 1). In some embodiments, performing activity 802 can comprise an activity of providing at least part of multiple sensor devices. Each sensor device of the multiple sensor device(s) can be similar or identical to sensor device(s) 106 (FIG. 1).

Further still, method 800 can comprise activity 803 of providing a neutron conversion layer, such as, for example, over the device layer. The neutron conversion layer can be similar or identical to neutron conversion layer 104 (FIG. 1). In some embodiments, activity 803 can be omitted.

Also, method 800 can comprise activity 804 of providing a moderator layer, such as, for example, over the neutron conversion layer. The moderator layer can be similar or identical to moderator layer 105 (FIG. 1). In some embodiments, activity 804 can be omitted.

In some embodiments, method 800 can comprise activity 805 of providing an analog-to-digital conversion (ADC) module. The ADC module can be similar or identical to ADC module 117 (FIG. 1).

In these embodiments, method 800 can comprise activity 806 of coupling the ADC module to the device layer. In some embodiments, activity 805 and/or activity 806 can be omitted.

Figure 9:
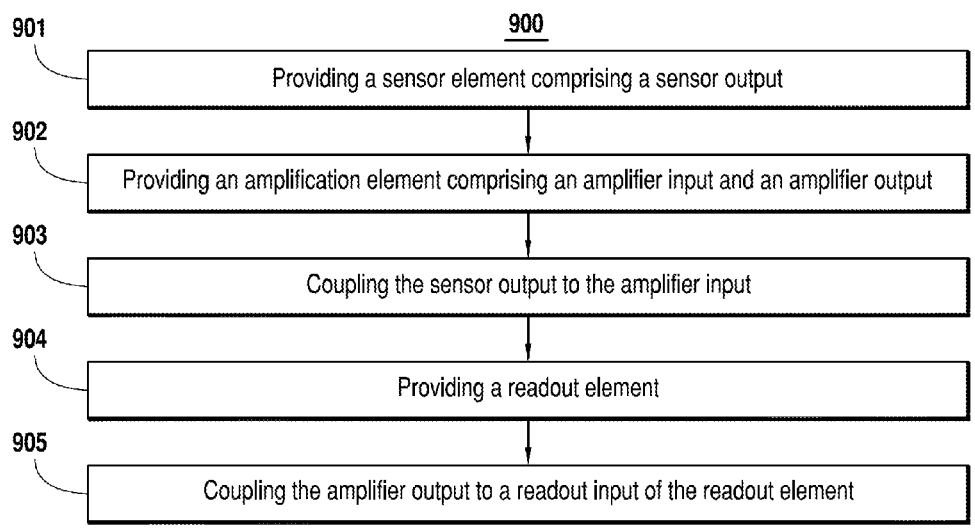
FIG. 9 illustrates a flow chart for an embodiment of a method of providing a sensor device.

Turning ahead in the drawings, FIG. 9 illustrates a flow chart for method 900 of providing a sensor device, according to an embodiment. Method 900 is merely exemplary and is not limited to the embodiments presented herein. Method 900 can be employed in many different embodiments or examples not specifically depicted or described herein. In some embodiments, the activities, the procedures, and/or the processes of method 900 can be performed in the order presented. In other embodiments, the activities, the procedures, and/or the processes of method 900 can be performed in any other suitable order. In still other embodiments, one or more of the activities, the procedures, and/or the processes in method 900 can be combined or skipped. In many embodiments, the sensor device can be similar or identical to sensor device 207 (FIG. 2).

In some embodiments, performing activity 802 (FIG. 8) can comprise performing at least part of method 900 one or more times. In these embodiments, method 900 can be performed multiple times approximately simultaneously with each other.

Method 900 can comprise activity 901 of providing a sensor element comprising a sensor output. In many embodiments, the sensor element can be similar or identical to sensor element 208 (FIG. 2), and the sensor output can be similar or identical to sensor output 211 (FIG. 2). In some embodiments, performing activity 901 can comprise an activity of providing a PIN diode and/or a photodiode.

Figure 10:
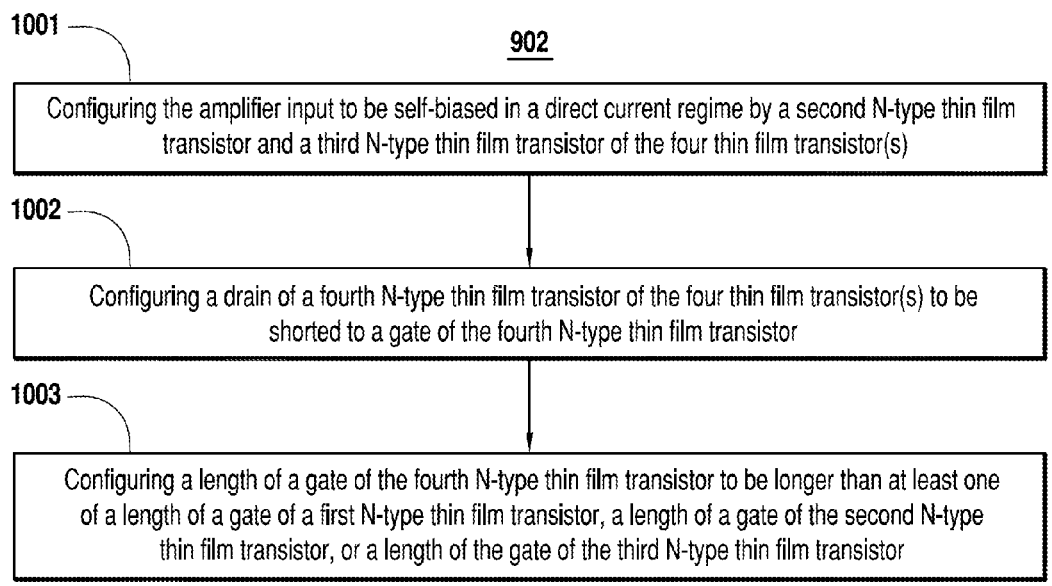
FIG. 10 illustrates an exemplary activity of providing an amplification element comprising an amplifier input and an amplifier output where the activity comprises providing at least four thin film transistors (e.g., N-type thin film transistors) for each amplification stage of the amplification stage(s), according to the embodiment of FIG. 9.

Further, method 900 can comprise activity 902 of providing an amplification element comprising an amplifier input and an amplifier output. In many embodiments, the amplification element can be similar or identical to amplification element 209 (FIG. 2) and/or amplification element 309 (FIG. 3). Meanwhile, the amplifier input can be similar or identical to amplifier input 212 (FIG. 2), and the amplifier output can be similar or identical to amplifier output 213 (FIG. 2). In some embodiments, performing activity 902 can comprise an activity of providing at least one amplification stage. Further, performing this activity can comprise an activity of providing at least four thin film transistors (e.g., N-type thin film transistors) for each amplification stage of the amplification stage(s). The amplification stage(s) can be similar or identical to amplification stage(s) 318 (FIG. 3). Further, the four thin film transistors can be similar or identical to the thin film transistors of amplification stage(s) 318, such as, for example, first N-type thin film transistor 323, second N-type thin film transistor 324, third N-type thin film transistor 325, and fourth N-type thin film transistor 326. FIG. 10 illustrates an exemplary activity 902 where performing activity 902 comprises an activity of providing at least four thin film transistors (e.g., N-type thin film transistors) for each amplification stage of the amplification stage(s).

For example, activity 902 can comprise activity 1001 of configuring the amplifier input to be self-biased in a direct current regime by a second N-type thin film transistor and a third N-type thin film transistor of the four thin film transistor(s).

Further, activity 902 can comprise activity 1002 of configuring a drain of a fourth N-type thin film transistor of the four thin film transistor(s) to be shorted to a gate of the fourth N-type thin film transistor.

Further still, activity 902 can comprise activity 1003 of configuring a length of a gate of the fourth N-type thin film transistor to be longer than at least one of a length of a gate of a first N-type thin film transistor, a length of a gate of the second N-type thin film transistor, or a length of the gate of the third N-type thin film transistor.

Referring back to FIG. 9, method 900 can comprise activity 903 of coupling the sensor output to the amplifier input. In general, activity 903 can be performed after performing activities 901 and 902. In some embodiments, activity 903 can be performed as part of activity 901 and/or activity 902.

In some embodiments, method 900 can comprise activity 904 of providing a readout element. The readout element can be similar or identical to readout element 210 (FIG. 2), readout element 410 (FIG. 4), and/or readout element 510 (FIG. 5).

Further, in these embodiments, method 900 can comprise activity 905 of coupling the amplifier output to a readout input of the readout element. The readout input can be similar or identical to readout input 214 (FIG. 2).

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that one or more of the activities of method 800 (FIG. 8) and method 900 (FIG. 9) may be comprised of many different activities, procedures and be performed by many different modules, in many different orders that any element of FIGS. 1-13 may be modified and that the foregoing discussion of certain of these embodiments does not necessarily represent a complete description of all possible embodiments.

Generally, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system comprising:
a sensor device comprising:
   a sensor element comprising a sensor output; and
   an amplification element comprising multiple amplification stages, an amplifier input, and an amplifier output;
   wherein:
   the sensor output is coupled to the amplifier input;
   each amplification stage of the multiple amplification stages comprises at least four thin film transistors, an input node, and an output node;
   the sensor element is configured to detect at least one of a physical quantity or an event and to provide an electric signal to the amplification element in response to detecting the at least one of the physical quantity or the event;
   the amplification element is configured to amplify the electric signal received from the sensor element;
   the at least four thin film transistors comprise at least four N-type thin film transistors;
   the at least four N-type thin film transistors comprise a first N-type thin film transistor, a second N-type thin film transistor, a third N-type thin film transistor, and a fourth N-type thin film transistor;
   each N-type thin film transistor of the at least four N-type thin film transistors comprises a gate, a source, and a drain;
   for the each amplification stage of the multiple amplification stages:
      the source of the third N-type thin film transistor is directly coupled to the gate and the drain of the second N-type thin film transistor so that the second N-type thin film transistor and the third N-type thin film transistor are coupled in series with each other; and
      the source of the second N-type thin film transistor is directly coupled to the input node;
   the multiple amplification stages comprise at least two amplification stages coupled in series;
   adjacent amplification stages of the at least two amplification stages each are coupled together in series by at least one amplifier capacitor;
   the multiple amplification stages comprise a first amplification stage and a final amplification stage;
   the amplifier input comprises the input node of the first amplification stage; and
   the amplifier output comprises the output node of the final amplification stage.

2. The system of claim 1 wherein:
the sensor element comprises a PIN diode.

3. The system of claim 1 wherein:
for each amplification stage of the multiple amplification stages:
   the gate for the first N-type thin film transistor is directly coupled to the input node;
   the drain for the third N-type thin film transistor is directly coupled to the output node; and
   the source for the fourth N-type thin film transistor is directly coupled to the output node.

4. The system of claim 1 wherein:
the amplifier input is self-biased in a direct current regime by the second N-type thin film transistor and the third N-type thin film transistor.

5. The system of claim 1 wherein:
the at least two amplification stages coupled in series comprise at least three amplification stages coupled in series;
the at least three amplification stages comprise the first amplification stage, the final amplification stage, and a second amplification stage;
the output node of the first amplification stage is coupled in series to the input node of the second amplification stage by a first amplifier capacitor; and
the output node of the second amplification stage is coupled in series to the input node of the final amplification stage by a second amplifier capacitor.

6. The system of claim 1 further comprising:
a row access transistor; and
one of:
   (a) a unity gain buffer and a column reset transistor, wherein the unity gain buffer and the column reset transistor are coupled to the row access transistor; or
   (b) a current integrator and a source follower element comprising a source follower element capacitor and a source follower transistor coupled to the row access transistor, wherein the source follower element capacitor couples the source follower transistor to the amplifier output and the row access transistor is coupled to the current integrator.

7. The system of claim 1 further comprising:
a flexible substrate; and
a device layer over the flexible substrate;
wherein:
the device layer comprises at least part of multiple sensor devices; and
the multiple sensor devices comprise the sensor device.

8. The system of claim 7 further comprising:
a neutron conversion layer over the device layer.

9. The system of claim 8 wherein:
the neutron conversion layer comprises at least one of 10-Boron or 6-Lithium.

10. The system of claim 8 further comprising:
a moderator layer over the neutron conversion layer.

11. The system of claim 1 wherein:
the drain of the fourth N-type thin film transistor is shorted to the gate of the fourth N-type thin film transistor.

12. The system of claim 1 wherein:
a length of the gate of the fourth N-type thin film transistor is longer than at least one of a length of the gate of the first N-type thin film transistor, a length of the gate of the second N-type thin film transistor, or a length of the gate of the third N-type thin film transistor.

13. A method of providing a system, the method comprising:
providing a sensor device;
wherein:
providing the sensor device comprises:
providing a sensor element comprising a sensor output;
providing an amplification element comprising an amplifier input and an amplifier output; and
coupling the sensor output to the amplifier input;
providing the amplification element comprises providing multiple amplification stages;
providing the multiple amplification stages comprises:
for each amplification stage of the multiple amplification stages:
providing at least four N-type thin film transistors, the at least four N-type thin film transistors comprising a first N-type thin film transistor, a second N-type thin film transistor, a third N-type thin film transistor, and a fourth N-type thin film transistor, and each N-type thin film transistor of the at least four N-type thin film transistors comprising a gate, a source, and a drain;
providing an input node and an output node;
directly coupling the source of the third N-type thin film transistor to the gate and the drain of the second N-type thin film transistor so that the second N-type thin film transistor and the third N-type thin film transistor are coupled in series with each other; and
directly coupling the source of the second N-type thin film transistor to the input node; and
coupling together in series at least two amplification stages of the multiple amplification stages;

coupling together in series the at least two amplification stages of the multiple amplification stages comprises:
coupling together in series adjacent amplification stages of the at least two amplification stages of the multiple amplification stages by at least one amplifier capacitor;
the multiple amplification stages comprise a first amplification stage and a final amplification stage;
the amplifier input comprises the input node of the first amplification stage;
the amplifier output comprises the output node of the final amplification stage;
the sensor element is configured to detect at least one of a physical quantity or an event and to provide an electric signal to the amplification element in response to detecting the at least one of the physical quantity or the event; and
the amplification element is configured to amplify the electric signal received from the sensor element.

14. The method of claim 13 wherein:
providing the sensor element comprises providing a PIN diode.

15. The method of claim 13 wherein:
providing the at least four N-type thin film transistors comprises:
configuring the amplifier input to be self-biased in a direct current regime by the second N-type thin film transistor and the third N-type thin film transistor;
configuring the drain of the fourth N-type thin film transistor to be shorted to the gate of the fourth N-type thin film transistor; and
configuring a length of the gate of the fourth N-type thin film transistor to be longer than at least one of a length of the gate of the first N-type thin film transistor, a length of the gate of the second N-type thin film transistor, or a length of the gate of the third N-type thin film transistor.

16. The method of claim 13 further comprising:
providing a flexible substrate; and
providing a device layer over the flexible substrate;
wherein:
providing the device layer comprising providing at least part of multiple sensor devices; and
providing the at least the part of the multiple sensor devices comprises providing at least part of the sensor device.

17. The method of claim 16 further comprising:
providing a neutron conversion layer over the device layer; and
providing a moderator layer over the neutron conversion layer.

18. A system comprising:
a flexible substrate; and
a device layer over the flexible substrate, the device layer comprising at least part of multiple sensor devices;
wherein:
each sensor device of the multiple sensor devices comprises:
a sensor element comprising a sensor output; and
an amplification element comprising multiple amplification stages, an amplifier input, and an amplifier output;
the at least the part of the multiple sensor devices comprises the sensor element and the amplification element;
the sensor output is coupled to the amplifier input;

each amplification stage of the multiple amplification stages comprises an input node, an output node, and at least four N-type thin film transistors comprising a first N-type thin film transistor, a second N-type thin film transistor, a third N-type thin film transistor, and a fourth N-type thin film transistor;

the sensor element is configured to detect at least one of a physical quantity or an event and to provide an electric signal to the amplification element in response to detecting the at least one of the physical quantity or the event;

the amplification element is configured to amplify the electric signal received from the sensor element;

the sensor element comprises a PIN diode;

each N-type thin film transistor of the at least four N-type thin film transistors comprises a gate, a source, and a drain;

for each amplification stage of the multiple amplification stages:
  the source of the third N-type thin film transistor is directly coupled to the gate and the drain of the second N-type thin film transistor so that the second N-type thin film transistor and the third N-type thin film transistor are coupled in series with each other;
  the source of the second N-type thin film transistor is directly coupled to the input node;
  the gate for the first N-type thin film transistor is directly coupled to the input node;
  the drain for the third N-type thin film transistor is directly coupled to the output node;
  the source for the fourth N-type thin film transistor is directly coupled to the output node;
  the drain of the fourth N-type thin film transistor is shorted to the gate of the fourth N-type thin film transistor; and
  a length of the gate of the fourth N-type thin film transistor is longer than at least one of a length of the gate of the first N-type thin film transistor, a length of the gate of the second N-type thin film transistor, or a length of the gate of the third N-type thin film transistor;

the multiple amplification stages comprise three amplification stages coupled in series;

adjacent amplification stages of the three amplification stages each are coupled together in series by at least one amplifier capacitor, respectively;

the three amplification stages comprise a first amplification stage and a final amplification stage;

the amplifier input comprises the input node of the first amplification stage; and the amplifier output comprises the output node of the final amplification stage.

19. The system of claim 18 wherein:
the physical quantity comprises a charge; and
the event comprises receipt of ionizing radiation.

20. The method of claim 17 wherein:
the neutron conversion layer comprises 10-Boron.

21. The method of claim 17 wherein:
the neutron conversion layer comprises 6-Lithium.

* * * * *